US005084679A

United States Patent [19]

Löfgren

[11] Patent Number: 5,084,679

[45] Date of Patent: Jan. 28, 1992

[54] LEAKAGE DETECTOR USING SLOTTED INSULATED CONDUCTORS

[76] Inventor: Stig T. H. Löfgren, Masvägen 16, 183 51 Täby, Sweden

[21] Appl. No.: 618,593

[22] Filed: Nov. 28, 1990

Related U.S. Application Data

[63] Continuation of Ser. No. 11,633, Feb. 6, 1987, abandoned.

[30] Foreign Application Priority Data

Feb. 6, 1986 [SE] Sweden ................................ 8600532

[51] Int. Cl.[5] ........................ G01R 31/08; G08B 21/00

[52] U.S. Cl. ................................ 324/525; 174/11 R; 340/605

[58] Field of Search ................ 324/525, 526; 340/604, 340/605, 584; 174/11 R

[56] References Cited

U.S. PATENT DOCUMENTS 2,056,085 9/1936 Alles ................................ 174/11 R
2,326,557 8/1943 Peirce ................................ 174/11 R
3,098,116 7/1963 Jore et al. ................................ 340/604
3,365,661 1/1968 Zimmerman ................................ 324/526
3,588,689 6/1971 Crawford ................................ 324/526
4,594,638 6/1986 Suzuki et al. ................................ 174/11 R
4,677,371 6/1987 Imaizumi ................................ 174/11 R

*Primary Examiner*—Kenneth A. Wieder
*Assistant Examiner*—Maura K. Regan
*Attorney, Agent, or Firm*—Burns, Doane, Swecker & Mathis

[57] ABSTRACT

A detector for use in a detecting device determines the occurrence of a change in the conductivity of a medium includes electrical conductors. The respective electrically insulated conductors are prepared at predetermined, restricted locations thereon in order to expose parts of the conductor material. The electrical conductors are provided as two or more twined or twisted conductors which are electrically insulated from one another. The electrically insulated layer is removed from the outermost parts of the conductors with the aid of a mechanical working process.

19 Claims, 1 Drawing Sheet

7
6
40
10
11
13
12
8
4a'
4b'
9

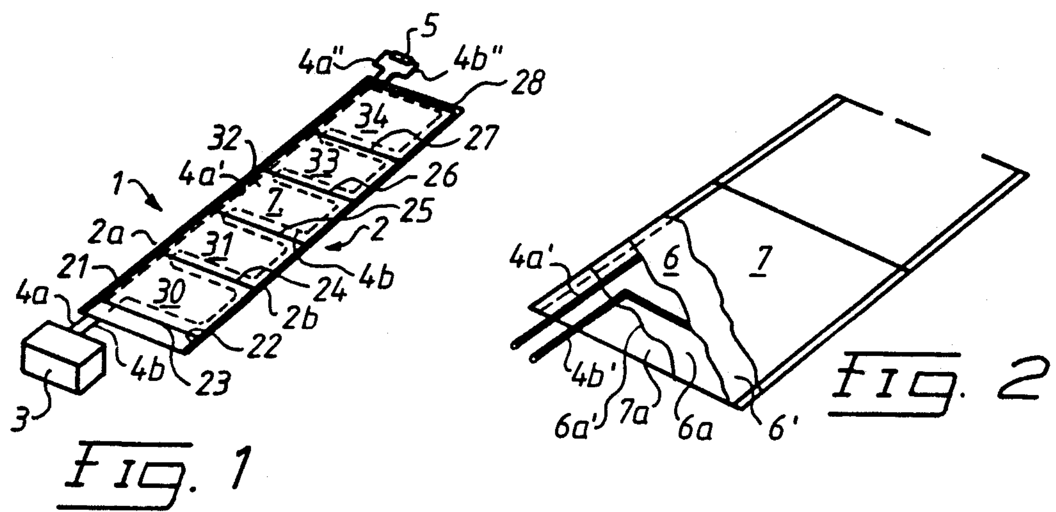
Fig. 1
Fig. 2
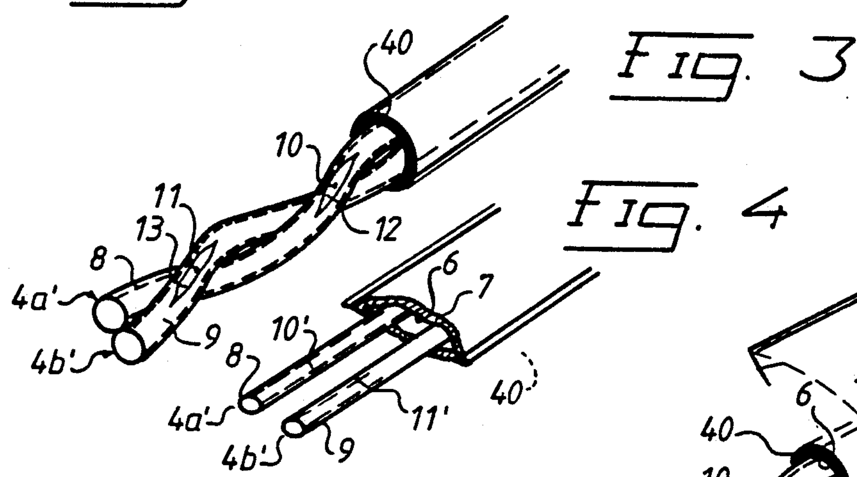
Fig. 3
Fig. 4
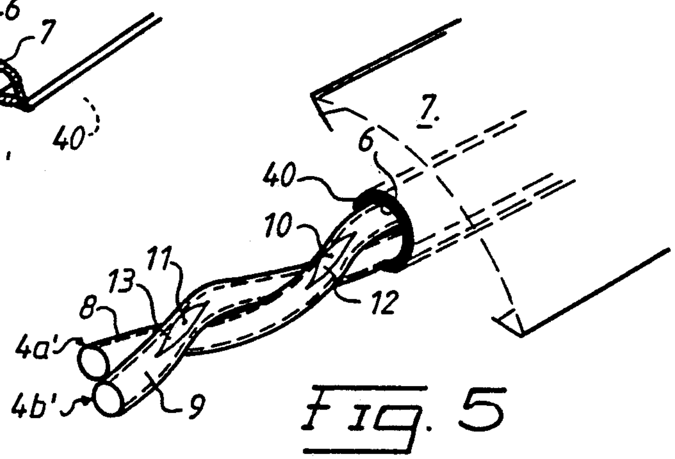
Fig. 5
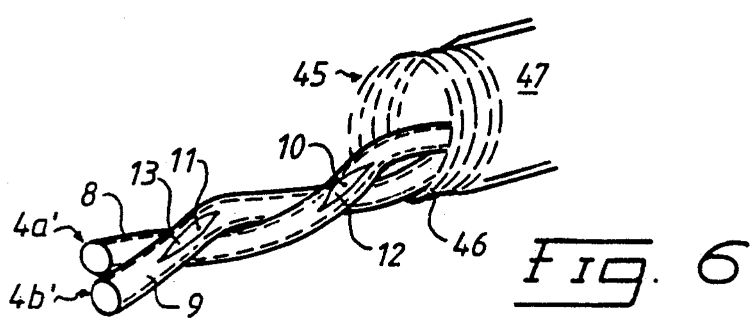
Fig. 6

LEAKAGE DETECTOR USING SLOTTED INSULATED CONDUCTORS

This application is a continuation of application Ser. No. 011,633, filed Feb. 6,1987, now abandoned.

TECHNICAL FIELD

The present invention relates to a detector of the kind which comprises, inter alia, at least one, normally several, electrical conductors and which is intended for use in detection devices in order to establish changes in the electrical conductivity of a medium surrounding the detector.

The change in the conductivity of the medium may be caused by moistening of a material with water, oil, synthetic fluid or the like, by admixture of the medium with a gas, mist or the like which causes a change in conductivity, and/or by subjecting the medium and/or the material to temperature changes, normally an increase in temperature.

For the sake of simplicity, the following description will be made solely with reference to one of these variants, namely a moisture detecting device, apparatus or system, and with reference to water as the moisture source.

The invention thus relates to a detector comprising one or more conductors or conductor parts which are fabricated from an electrically conductive material and which have located therebetween a moisture absorbant material, the conductivity of which is changed, increased, when taking up moisture.

The moisture detecting device also incorporates electrical and/or electronic devices or circuits for evaluating changes in conductivity of the material.

BACKGROUND PRIOR ART

The Swedish Patent Specification Number 8204814-3, Publication Number 375 395, describes and illustrates an alarm device which incorporates detecting means in the form of electric conductors which are intended to co-act with a material whose conductivity changes when absorbing moisture, wherewith a change in conductivity between the conductors results in a change in electrical resistance or in the transition of the device from a normal, or passive, state to an active alarm state, thereby producing an alarm signal. The alarm device includes one or more trigger circuits, to which the outputs of respective associated conductors are connected.

Thus, it is known that in a normal passive state of the alarm device a pre-determined resistance and/or impedance shall prevail between associated conductors. It is also known that a given lower resistance and/or impedance shall prevail between associated conductors in the active alarm state of the device.

It is also known to incorporate in the detecting device a control circuit which, under the influence of pulses, brings the trigger circuits to an operational state in which they will react in response to said pre-determined prevailing impedance values and initiate an alarm. It is also known for the length of the pulse produced by the control circuit to be shorter than the time taken for the alarm device to react from the moment of activation to the moment at which the alarm is produced.

A number of mutually different detectors for detecting devices of this kind and for similar devices are known the art.

One example of these known detectors is found in U.S. Patent No. 2 049 321.

This U.S. Patent teaches an alarm device which incorporates a first conductor and a second conductor, said conductors being bared, or stripped, of insulation, at each detection location, so that a plate can be urged by means of a spring against a formed loop.

This U.S. specification teaches the possibility of triggering a part with the aid of moisture, such as water.

The U.S. Pat. No. 3 662 367 teaches the use of twined or plied conductors, of which one of the conductors is a plastic tube and the other is a paperinsulated electric conductor.

The platic tube is provided at pre-determined locations therealong with windows which permit moisture to pass through and wet the insulation.

SUMMARY OF THE INVENTION

Technical Problems

With reference of the prior state of the art, as expressed in the aforegoing, it will be seen that one qualified technical problem resides in the provision of an efficient moisture detecting device with the aid of simple means.

It will also be seen that another technical problem resides in the provision of conditions which will enable a detector assembly of basic construction to be used in its basic form and also in a modified form, normally to detect the presence of moisture under mutually different conditions and in connection with varying technical fields.

Another qualified technical problem in this art, in view of the present state of the art as illustrated above, resides in the provision of a detector which incorporates one or more conductors or parts comprising electrically conductive material, and in which there is located between the conductors a moisture absorbing material having a wide covering surface which when moisture is absorbed results in a change in the conductivity of the material, and which will enable the detector to have the form of a mat, and to enable the mat to be produced from simple means.

Another technical problem is one of providing a moisture detector which will rapidly produce an alarm even when only a small quantity of moisture acts on a wide surface or area.

A further technical problem in this regard is one of providing a detector which has a wide covering surface and in which the electrical conductors used can be spaced widely apart, while still being highly sensitive to relatively small quantities of moisture.

Another technical problem is one of providing a detector which comprises an outer surface which protects the detector against damage and which is solely effective in permitting moisture to pass therethrough, and in which detector there is located around or adjacent the conductors, which when moistened experience a change in conductivity, a moisture permeable material which is capable of absorbing and/or dispersing moisture.

Another technical problem is one of creating conditions which will enable the different materials selected to be readily joined together, particularly with regard to the welding of thermoplastic materials, e.g. butt welding, etc.

Another technical problem is one of providing conditions which will enable the undersurface of the detector to be made of a moisture impermeable material to which the remaining material can be joined.

A further technical problem resides in the provision of conditions which will enable a detector to be produced, with the aid of simple means, in the form of a web incorporating discrete sections each of which is separated from an adjacent section with the aid of one or more welding lines or leads, thereby enabling a measurable change in conductivity to be produced rapidly with the aid of the restricted presence of moisture.

Still another technical problem in this field is one of providing for use with a moisture detecting device, preferably of the aforesaid kind, a detector which can be produced from at least one, preferably two or more, mutually electrically insulated narrow electric conductors, thereby to form an elongated narrow tube or strip, while using herefor a highly moisture-absorbent material which, when absorbing moisture, causes a change in the conductivity of the conductors in contact therewith.

When using electrical conductors provided with an electrically insulating layer, a further technical problem resides in exposing the conductor material, mechanically or in some other way, at pre-determined restricted parts thereof, so that a change in conductivity between the thus exposed conductor parts can be detected and evaluated.

In the case of electrical conductors which comprise two conductors which are twined together and/or mutually parallel with one another and electrically insulated relative to one another, a further technical problem resides in providing conditions which will enable the electrical insulating layer to be removed solely from the outermost parts of the conductors, with the aid of simple means, under the condition that an exposed part of one conductor is electrically insulated from an exposed part of the other conductor.

In the case of a detector of the aforesaid kind, a further technical problem resides in the provision of conditions which enable the electric conductors to be encased by a first, external material which will solely permit moisture to penetrate therethrough and which is intended to protect the whole of the detector against damage, and to incorporate a second, inner material which is highly permeable to moisture and which will absorb and/or disperse said moisture, particularly adjacent those conductor parts which are exposed, and in which primarily only the inner material results in the desired change in conductivity in the presence of moisture.

A further technical problem prevailing in a detector of the aforesaid kind is one of providing conditions which will enable the first outer material to comprise a plastics material, and the inner material to comprise a plastic-coated tissue paper, such that these materials can be readily joined or fastened to one another by means of heat welding processes or the like.

A further technical problem in this regard is one of providing conditions which will enable the conductor to be coated with a layer of material which will dissolve in oil products, therewith to cause the desired increase in conductivity.

SOLUTION

The present invention relates to a detector for use in detecting devices and intended to establish the occurrence of a change in the conductivity of a medium, the detector comprising one or more electrical conductors.

The electrical conductors comprise an electrically conductive material enclosed in an electrically insulating layer.

The electrically insulating layer is machined and/or prepared at pre-determined, restricted locations along the conductor, in order to expose the electrically conductive material.

In accordance with the invention the electrically insulating layer is worked mechanically and/or prepared in a manner to produce a penetrating slot which extends in the axial direction of the conductor and/or to produce in the insulating layer a number of discrete penetrations located in spaced relationship along the axis of said conductor, the slot and/or discrete penetrations being formed in a manner such that the electrically insulating layer defining said slot and/or penetrations extends around the conductive material from the mutually opposing edges of the slot and/or penetrations.

In accordance with one preferred embodiment of the invention the electrical conductors comprise two conductors which are electrically insulated from one another and twined together and/or extend parallel with one another; and in that the electrically insulating layer is removed mechanically from solely the outermost parts of the conductor, e.g. by milling, grinding or some like mechanical process.

In accordance with one embodiment of the invention the electrical conductors comprise two or more conductors which are insulated electrically from one another and. twined together; and in that the electrically insulating layer is removed mechanically from solely the outermost parts of the twined conductors.

It is proposed in accordance with the invention that at least the exposed conductor parts are re-insulated electrically with a layer of soluble medium, said medium comprising a substance which when dissolved will greatly change, e.g. increase, the conductivity of the material located between adjacent exposed parts.

In accordance with another embodiment of the invention a first outer material has the pronounced ability of solely permitting moisture to pass therethrough, while a second, inner material has the pronounced ability of permitting moisture to pass through and to disperse moisture, the first, outer material comprising a plastics material, and the second, inner material comprising a plastic-coated tissue paper, these materials being welded together.

It is also proposed that material applied around the conductor and being in electrical contact with exposed parts is treated in a manner which will result in a change in the electrical conductivity of the material in the presence of moisture, e.g. by coating the electric conductor with an electrically insulating varnish or the like at discrete locations thereon.

In accordance with one advantageous embodiment of the invention the conductor is shielded against moisture absorption and the conductivity of the space located between exposed parts is changed when the level of liquid rises above the conductor material.

In accordance with a further embodiment of the invention the conductors and/or their exposed parts are coated with a substance which will dissolve in oil products or synthetic products, there being provided a substance having conductivity changing properties and being soluble in oil products or synthetic products.

The material comprises a first material and a second material, the electric conductors being enclosed in the second material.

The electrical conductors are conveniently laid in a sinusoidal path within one section separated from an adjacent section.

The insulation assigned to the conductor is also arranged to form exposed parts or to form parts of changed conductivity, due to changes in temperature (increased temperature).

Finally, in accordance with another embodiment of the invention, discrete localities are arranged in mutually spaced relationship along the axis of the conductor and with two localities belonging to one and the same conductor being located on a respective side of a locality belonging to each of the remaining conductors. The material is caused to contact the exposed conductor material through a slot and/or discrete penetrations.

ADVANTAGES

Those advantages primarily associated with a detecting device according to the invention, and then particularly with a detector for use in a moisture detecting device, reside in the provision of means which will enable the presence of moisture to be indicated rapidly, even when the moisture is present in only small quantities.

BRIEF DESCRIPTION OF THE DRAWINGS

The invention will now be described in more detail with reference to a number of embodiments of detectors which can be used in a moisture detecting device and with reference to the accompanying drawings in which;

FIG. 1 is a perspective view of a moisture detecting device comprising an electric and/or electronic circuit for evaluating changes in the electrical conductivity of a detector, and also illustrates a first embodiment of a detector;

FIG. 2 illustrates a somewhat larger scale than FIG. 1 of the basic construction of the detector, several parts being intentionally omitted from the illustration;

FIG. 3 is a perspective view of a second embodiment of a detector;

FIG. 4 is a perspective view of a third embodiment of a detector according to the invention;

FIG. 5 is a perspective view of a fourth embodiment of a detector according to the invention; and FIG. 6 is a perspective view of a fifth embodiment of a detector according to the invention.

DESCRIPTION OF PREFERRED EMBODIMENTS

In FIG. 1 the reference 1 indicates generally a moisture detecting device which comprises a detector 2 and electric and/or electronic means or circuits, incorporating a control unit 3, for evaluating a change in the conductivity of a material incorporated in the detector, by establishing a change in the resistance or impedance between the conductors 4*a* and 4*b*. The electrical circuit incorporating the conductors 4*a* and 4*b* is terminated with a fixed resistance 5, and a change, increase, in the conductivity of the material 6, due to the penetration of moisture, is detected by the unit 3 as a reduction in the resistance or impedance of the circuit 4*a*, 4*b*.

The electric and/or electronic control unit 3 may advantageously comprise the circuit illustrated and described in Swedish Patent Specification 78048014-3, Publication No. 375 395, and hence this control circuit will not be described in detail here. It can be mentioned, however, that an alarm is activated when a transition occurs from a high resistance value to a low resistance value between the conductors 4*a* and 4*b*.

Thus, the detector 2 of the FIG. 1 embodiment comprises one or more conductors 4*a*', 4*b*' or parts comprises an electronically conductive material. Arranged between the conductors is a material 6 (FIG. 2) capable of absorbing moisture and the conductivity of which will change, increase, when absorbing moisture.

The conductors 4*a*' and 4*b*' may comprise the detector illustrated in FIG. 3.

When drawing the conductors 4*a*' and 4*b*' through the detector 2, the conductors will lie closer together than illustrated in FIG. 1.

In the FIG. 1 embodiment the conductor 4*a*' extends along one edge part 2*a* of the detector 2 and is connected, via a conductor 4*a*'', to a fixed resistance 5. The conductor 4*b* is laid in a zig-zag pattern, or like wave pattern, in the material 6, and is connected to the fixed resistance 5 by a conductor 4*b*''. The conductor 4*b*' extends substantially along the other edge part 2*b* of the detector.

Alternatively, the conductor 4*a*' may be connected to a resistance 5 and the conductor 4*b*' connected to a further resistance (not shown), or the conductors may be connected to one another in a manner to form a loop.

The detector 2 has two weld beads 21 and 22, one bead 21 being positioned immediately adjacent the edge part 2*a* and the other bead 22 being positioned immediately adjacent the edge part 2*b*.

The detector also incorporates further weld beads 23–28 which define discrete sections 30–34.

According to the present invention, as best seen from FIG. 2, the material comprises a first material 7 and a second material 6, this latter material incorporating the electrical conductors 4*a*' and 4*b*'.

In accordance with the embodiment illustrated in FIG. 2 the first material comprises an upper outer layer 7 and a lower outer layer 7*a*, while the second material comprises an upper inner layer 6 and a lower inner layer 6*a*.

The first outer layers of material 7, 7*a* have the pronounced ability solely of permitting moisture to pass therethrough, while the second, inner material layers comprise a material having a pronounced ability to permit moisture to penetrate and to absorb and/or disperse moisture.

Thus, it is proposed that the first outer material comprises a plastics material and the second inner material comprises a moisture absorbent material, preferably a tissue paper coated on one surface thereof with a plastics layer 6', 6*a*', i.e. the plastic coating faces away from the conductors 4*a*' and 4*b*'.

The plastic layer 6' and 6*a*' naturally comprises a coating which will ensure that moisture is able to penetrate to the moisture absorbent material 6, 6*a*.

It is conceivable for the material 7*a* to comprise a material which is totally resistant to moisture penetration. As a result hereof it is possible to join the upper, outer material 7, the upper inner material 6, the lower inner material 6*a* and the lower outer material 7*a* together in a single working operation, with the aid of weld lines, weld seams or the like.

FIG. 3 illustrates a second embodiment of a detector forming part of or used with a moisture detecting device, this detector also comprising electric conductors 4*a*', 4*b*' and a moisture absorbent material located between or around the conductors.

The detector according to FIG. 3 comprises two twined electrical conductors with an encasing material, to form an elongated rigid tube.

The encasing material may comprise a material 40 having the properties referred to with reference to the embodiment of FIG. 2 and the material 6. The material 40 comprises a woven textile tube impregnated with a substance which produces an increase in conductivity when moist.

In the embodiment according to FIG. 3 there is used two conductors 4*a*', 4*b*' which are insulated electrically relatively to one another with insulating layers 8 and 9 respectively, in which pre-determined restricted parts or locations 10, 11 are formed, preferably by mechanical processes, in order to expose conductor material 12, 13. The thus processed conductors and parts will be embraced by the material 40, and the material 40 is preferably in electrical contact with the exposed conductor parts 10, 11.

When the electrical conductors have the form of two twined conductors 4*a*', 4*b*' electrically insulated from one another the electrically insulating layer can be removed moved from the outermost parts by mechanical processes, such as milling, grinding or the like.

For example, twined or twisted electric conductors can be passed over a guide pulley and a grinding wheel located at a pre-determined distance from the periphery of the guide pulley can be caused to remove insulating material and some material at the locations 10 and 11. The thus prepared conductors are then enclosed with a material 40.

At least the exposed parts of the conductors may be covered with an electrically insulating layer which will dissolve in contact with moisture, this layer advantageously comprising a substance capable of significantly changing or increasing the conductivity of the material when said substance is dissolved in contact with moisture.

During manufacture respective electrical conductors can be provided at discrete locations thereon with an electrically insulating varnish or coating.

Respective electrical conductors and/or exposed parts may be coated with a material which dissolves in oil products.

In accordance with one preferred embodiment there is used a material which becomes more conductive when dissolved in oil products (admixed coal powder).

The insulation around the conductor may also be arranged to form exposed parts as a result of temperature changes, normally an increase in temperature.

FIG. 4 illustrates an embodiment which comprises two conductors 4*a*' and 4*b*' in mutually parallel, side-by-side relationship and covered with an electrically insulating layer 8, 9. Each insulating cover has a slot 10' and 11' formed therealong. The device illustrated in FIG. 4 also incorporates a first material 7 and a second material 6 which exhibit the same properties as the materials described with reference to FIG. 2, or a material 40 which exhibits the same properties as the material described with reference to FIG. 3.

FIG. 5 illustrates an embodiment in which a detector according to FIG. 3 is inserted between two materials 6 and 7 having the properties described with reference to FIG. 7.

FIG. 6 illustrates an embodiment in which the two twined conductors 4*a*' and 4*b*', according to FIG. 3 but with the absence of the material 40, are placed in a tubular member 45 comprising a helically wound wire 46. The wire is embraced by a material 47 having the ability to prevent water from collecting around the conductors in the event of the device coming into contact with water. Should the material casing 47 be subjected to water contact over a long period of time, however, water will penetrate through the material 47 and rise above the conductors 4*a*' and 4*b*', thereby to connect the exposed parts 10, 11 electrically to one another.

In accordance with a further embodiment of the invention the two conductors may be formed from mutually different materials, so that any moisture present will form a galvanic element between the conductors, the resultant voltage being detected in a control device.

Finally, the electrical conductors may be printed on a sheet of material, for example by means of a silkscreen printing process, and an electrically insulating material can be applied in a manner to leave certain parts of the conductors exposed.

The material can also be prepared to exhibit high conductivity in the presence of moisture.

It will be understood that the device according to the present invention will operate satisfactorily if solely one electric conductor is introduced into a metal tube or the like and if means are provided for producing a current path between the single conductor and the metal of the tube itself.

The invention is not restricted to the aforesaid embodiment since modifications can be made within the scope of the invention as defined in the following claims.

Finally it should be mentioned that the distance between the penetrated discrete locations 10 and 11 should be less than 100 mm. As this distance is depending upon the diameter of the conductor it is suggested that said distance is less than 100 times the diameter of the conductor, especially less than 50 times said diameter. It has been found that said distance normally shall be within the range of 10 to 30 times the diameter of the conductor.

I claim:

1. A detector for use in a detecting device for establishing a change in the conductivity of a medium, said detector consisting of electrical conductors having an electrically conductive material coated with an electrically insulating varnish at discrete regions and an electrically insulating layer substantially concentrically surrounding said material, and in which predetermined, portions of the insulating layer are prepared so as to expose the conductive material, said preparation of the insulating layer is effected to form in the insulating layer penetrating slots extending in the axial direction of the conductor material, said slots located in mutually spaced relationship in said axial direction, the slots being so formed that the electrical insulating layer adjacent thereof extends around said conductor material from the mutually opposing defining edges of said slots.

2. A detector according to claim 1, wherein at least the exposed parts of the conductors are coated with an electrically insulating layer which comprises a soluble medium which when dissolved changes its conductivity.

3. A detector according to claim 1, wherein a material applied around the conductor in electrical contact with the slots is treated so that the conductivity of the material changes when the material is moistened.

4. A detector according to claim 1, wherein the conductor is protected against moisture absorption, and the conductivity of the space between exposed conductor parts is changed when the level of water present rises above the conductor material.

5. A detector according to claim 1, wherein respective conductors and the slots are coated with a substance soluble in at least one of oil products and synthetic products.

6. A detector according to claim 5, wherein the detector further comprises a material having conductivity changing properties and is soluble in at least one of oil products and synthetic products.

7. A detector according to claim 1, wherein the insulation of the conductor is arranged to form exposed conductor parts of changed conductivity as a result of increased temperature.

8. A detector according to claim 1, wherein the electrical conductors comprise two or more twined conductors which are insulated electrically relative to one another; and in that solely the outermost parts of the twined conductors are bared of insulating material, said insulating material being removed by means of mechanical working processes.

9. A detector according to claim 8, wherein said discrete penetrating locations are arranged in mutually spaced relationship along the electrical conductor, with two locations on one conductor being located on a respective side of a location of each of the remaining conductors.

10. A detector according to claim 8, wherein the insulation of the conductor is arranged to form exposed conductor parts of changed conductivity as a result of increased temperature.

11. A detector according to claim 8, characterized in that it comprises a first, outer material (7, 7a) having a pronounced ability of solely permitting moisture to pass therethrough, and a second, inner material (6) having the pronounced ability of permitting moisture to pass therethrough and to disperse moisture.

12. A detector according to claim 11, characterized in that the first outer material comprises a plastic material, and the second, inner material comprises a plastic-coated tissue paper; and in that the two materials are welded together.

13. A detector according to claim 1 characterized in that it comprises a first, outer material (7, 7a) having a pronounced ability of solely permitting moisture to pass therethrough, and a second, inner material (6) having the pronounced ability of permitting moisture to pass therethrough and to disperse moisture.

14. A detector according to claim 13, characterized in that the first outer material comprises a plastics material, and the second, inner material comprises a plastic-coated tissue paper; and in that the two materials are welded together.

15. A detector according to claim 14, wherein the insulation of the conductor is arranged to form exposed conductor parts of changed conductivity as a result of increased temperature.

16. A detector according to claim 13, characterized in that the material comprises a first material and a second material, the electrical conductors being enclosed in said second material.

17. A detector according to claim 16, characterized in that one electrical conductor is laid in a wave-length pattern within a section separated from an adjacent section.

18. A detector according to claim 13, characterized in that the outer material is arranged to abut conductor material exposed by means of a slot and/or discrete locations.

19. A detector according to claim 13, wherein the insulation of the conductor is arranged to form exposed conductor parts of changed conductivity as a result of increased temperature.

* * * * *

UNITED STATES PATENT AND TRADEMARK OFFICE

CERTIFICATE OF CORRECTION

PATENT NO. : 5,084,679

DATED : January 28, 1992

INVENTOR(S) : Stig T.J. Löfgren

It is certified that error appears in the above-identified patent and that said Letters Patent is hereby corrected as shown below:

ON THE TITLE PAGE:

At [76] delete "Stig T.H. Löfgren" and insert ---Stig T.J. Löfgren--.

Signed and Sealed this

Eighth Day of June, 1993

Attest:

MICHAEL K. KIRK

Attesting Officer

Acting Commissioner of Patents and Trademarks